United States Patent
Fabian et al.

(10) Patent No.: US 7,464,713 B2
(45) Date of Patent: Dec. 16, 2008

(54) MINIATURE MAGNETOMECHANICAL TAG FOR DETECTING SURGICAL SPONGES AND IMPLEMENTS

(76) Inventors: Carl E. Fabian, 5001 London Walk, Miami, FL (US) 33138; Philip M. Anderson, III, 37 Winding Way, Madison, NJ (US) 07940; Gordon E. Fish, 103 Lorraine Ave., Upper Montclair, NJ (US) 07043

(*) Notice: Subject to any disclaimer, the term of this patent is extended or adjusted under 35 U.S.C. 154(b) by 180 days.

(21) Appl. No.: 10/723,566

(22) Filed: Nov. 26, 2003

(65) Prior Publication Data

US 2004/0129279 A1    Jul. 8, 2004

Related U.S. Application Data

(60) Provisional application No. 60/429,370, filed on Nov. 26, 2002.

(51) Int. Cl.
*A61B 19/00*    (2006.01)

(52) U.S. Cl. .................................................... 128/899

(58) Field of Classification Search ......... 128/897–899; 340/551, 552, 561, 567, 568, 572, 572.1, 340/572.6, 573.4; 324/201, 206; 343/6.8 R
See application file for complete search history.

(56) References Cited

U.S. PATENT DOCUMENTS

| | | | |
|---|---|---|---|
| 2,740,405 A | 4/1956 | Riordan | |
| 3,422,816 A | 1/1969 | Robinson et al. | |
| 3,587,583 A | 6/1971 | Greenberg | |
| 3,698,393 A | 10/1972 | Stone | |
| 3,820,103 A * | 6/1974 | Fearon | 340/572.2 |
| 4,114,601 A | 9/1978 | Abels | |
| 4,205,680 A | 6/1980 | Marshall | |
| 4,510,489 A | 4/1985 | Anderson et al. | |
| 4,658,818 A | 4/1987 | Miller, Jr. et al. | |
| 5,010,320 A * | 4/1991 | Cordery | 340/551 |
| 5,041,103 A | 8/1991 | Rupinskas | |
| 5,057,095 A | 10/1991 | Fabian et al. | |
| 5,105,829 A | 4/1992 | Fabian et al. | |
| 5,107,862 A | 4/1992 | Fabian et al. | |

(Continued)

*Primary Examiner*—Samuel G Gilbert
(74) *Attorney, Agent, or Firm*—Ernest D. Buff & Associates, LLC; Ernest D. Buff; Gordon E. Fish (57) ABSTRACT

Externally detectable electronic article surveillance markers are attached to surgical implements, such as sponges and surgical instruments, appointed for use in a surgical wound. The attachment mechanism facilitates detection by an external interrogating field before the wound has been closed and the patient has left the operating table. The markers are responsive to the imposition of an interrogating field produced by an electronic article surveillance system. Markers contain one or more magnetomechanically responsive elements that are urged into mechanical resonance by the interrogating field. The ring-down of the resonance and the associated dipolar electromagnetic field provide a signal-identifying characteristic detected by a detection system. Upon detection, an audible or visible signal is triggered to alert relevant medical personnel to the need for follow-up care and removal of the offending item. The resonance occurs at a frequency ranging from about 70 to 300 kHz. Misadventures during operative procedures—especially those wherein implements remain undiscovered at the time of surgery and are retained indefinitely within the surgical cavity, often entailing dire consequences to the patient—are virtually eliminated. The attachment mechanism and markers assure that surgical implements are reliably detected and removed before completion of the surgical procedure.

11 Claims, 4 Drawing Sheets

U.S. PATENT DOCUMENTS

| | | | |
|---|---|---|---|
| 5,188,126 A | 2/1993 | Fabian et al. | |
| 5,190,059 A | 3/1993 | Fabian et al. | |
| 5,329,944 A | 7/1994 | Fabian et al. | |
| 5,338,373 A * | 8/1994 | VonHoene et al. | 148/121 |
| 5,447,511 A | 9/1995 | Gadd | |
| 5,602,527 A * | 2/1997 | Suenaga | 340/551 |
| 5,664,582 A | 9/1997 | Szymaitis | |
| 5,854,589 A * | 12/1998 | How et al. | 340/551 |
| 5,891,270 A * | 4/1999 | Hasegawa | 148/304 |
| 6,097,312 A * | 8/2000 | Tanji et al. | 340/905 |
| 6,130,612 A * | 10/2000 | Castellano et al. | 340/572.6 |
| 6,359,563 B1 * | 3/2002 | Herzer | 340/572.6 |
| 6,407,676 B1 * | 6/2002 | Tanji et al. | 340/933 |
| 6,812,842 B2 * | 11/2004 | Dimmer | 340/572.4 |
| 7,075,440 B2 * | 7/2006 | Fabian et al. | 340/572.6 |
| 2002/0005783 A1 * | 1/2002 | Irizarry et al. | 340/572.1 |

* cited by examiner

MINIATURE MAGNETOMECHANICAL TAG FOR DETECTING SURGICAL SPONGES AND IMPLEMENTS

This application claims the benefit of U.S. Provisional Application No. 60/492,370, filed Nov. 26, 2002.

BACKGROUND OF THE INVENTION

1. Field of the Invention

The present invention relates to a system for detection of a surgical implement; and more particularly, to a system wherein a magnetomechanically resonant marker is attached to a surgical implement, thereby permitting the implement to be detected if inadvertently left within a patient during a surgical procedure.

2. Description of the Prior Art

During the course of a surgical operation it is generally necessary for a variety of articles, such as surgical sponges, gauzes, instruments and the like, to be placed into a wound cavity. Despite rigorous attention given to locating these items and ensuring removal of all of them prior to completion of the surgical procedure and closure of the surgical incision, such items are sometimes overlooked and remain within the patient. When this occurs, serious consequences often ensue. The patient may suffer pain, infection, intestinal obstruction, and even death. An additional invasive surgical procedure to remove the foreign object is essential to prevent serious, and possibly fatal, consequences to the patient. The severity of the problem of retained surgical implements has been recognized since the earliest days of surgery. The procedures traditionally employed to prevent post-surgical implement retention include manual search of the wound by the surgeon prior to closure and a careful accounting for all materials inserted and removed from the wound. This accounting function is customarily carried out by the operating room staff, usually the circulating nurse. Notwithstanding these precautionary measures the accidental retention of surgical implements continues to occur to this day with disturbing regularity, even in highly respected institutions. Surgeons and related medical professionals regard this eventuality as a major unsolved problem.

At present, physical count combined with manual search remains the primary protocol used for detecting retained surgical implements. Nevertheless, the above-mentioned shortcomings of the protocol have led to other approaches, such as the use of x-ray methods. Most surgical instruments are composed of metal, and are easily visible on x-ray. Sponges are generally made to bear a radiopaque component to make them also visible on x-ray. However, intraoperative x-rays are not routinely performed before closure of the incision for several reasons: They entail the risk of extension of operative time and anesthesia, along with undesirable expense, inconvenience, and radiation exposure. Postoperative x-rays are subject to some of the same disadvantages and are not routinely done unless there is a specific question or suspicion of a retained implement in a given case. Moreover, even when postoperative x-rays are obtained, retained surgical implements are still overlooked in many cases, owing to the presence of artifacts or other competing shadows on the film or the unfavorable orientation of the object relative to the direction of the incident x-ray beam and the position of the x-ray film. If a retained article is detected, a timely second operation is required to effect its removal, notwithstanding the further trauma to the patient. The severity of the problem clearly warrants efforts that allow the aforementioned consequences to be avoided altogether by ensuring removal of the offending articles before surgery is completed, not at a later point.

The problem of retained sponges is particularly severe. After use, a sponge is generally soaked with blood or other bodily fluids, making it difficult for the surgeon to spot against the background of the fluids and body structures within the surgical cavity. Surgical sponges about 45 cm (18 inches) square are used in virtually all major abdominal surgeries, and are the surgical item most frequently overlooked. Accordingly, a single method and system by which this and other surgical items can be reliably detected in a surgical cavity would afford a significant improvement in the safety of surgery.

Over the years many efforts have been made to prevent the accidental retention of surgical implements. U.S. Pat. Nos. 5,057,095, 5,107,862, 5,190,059, 5,329,944, 5,105,829, and 5,188,126 to Fabian et al. disclose the use of various technologies to detect surgical implements marked with a tag and left within the surgical wound after completion of surgery and prior to closing the wound. Despite these and other disclosures, the use of externally detectable markers has not yet become a part of routine hospital practice. Among the remaining impediments are the size and physical characteristics of known marker tags to which present detection systems are reliably responsive.

Suitable systems and the associated markers must satisfy a number of requirements. There must be reliable and convenient means of affixing such markers to surgical items. Any item used invasively must be capable of being appropriately sanitized and sterilized prior to use. The size and physical characteristics of the attached tag must not compromise the functionality of the surgical item or unduly restrict the ability of the surgeon or other assistant to see and access the operation site and to manipulate and use the item in an optimal manner for its intended primary function. The item should not harm the patient and should be compatible with the surgical environment and not be degraded in the presence of bodily fluids and other substances encountered during surgery.

The markers required for presently available surgical implement detection systems are of a size that precludes their attachment to many commonly used implements. Systems employing markers that are smaller and lighter, without a concomitant reduction in the detectability of marked, retained instruments are thus highly sought.

SUMMARY OF THE INVENTION

The present invention provides a surgical implement detection system for detecting surgical implements within a wound at the conclusion of a surgical procedure. A wide variety of implements used in the course of surgery may be tagged with a magnetomechanically resonant marker, in accordance with the present invention. Following surgery, the patient is scanned using an external detection system. Any tagged implements inadvertently retained in the wound may be identified immediately, allowing follow-up medical care and removal of the item, thereby averting serious and potentially fatal consequences for the patient.

The surgical implements that may be marked and detected notably include surgical sponges and surgical instruments. As used herein, the term "surgical sponge" refers to a variety of fabric-type articles used to protect body tissues and to absorb blood and other fluids and substances encountered during surgery. Surgical sponges are typically planar and square or rectangular in shape and are generally comprised of a plurality of layers of woven or non-woven fabric. The fabric may be composed of either natural fibers like cotton or synthetics including nylon, rayon, polyester, and acrylics. The sponge optionally comprises non-absorbent surface layers and absorbent interior layers. Sponges are widely used during surgical procedures to absorb blood and other bodily fluids present in the surgical field and as a protective interface between an organ (or other internal body part) and surgical instruments used to manipulate and secure the organ in a displaced position facilitating a surgeon's access to another body structure otherwise obscured. A sponge is also sometimes secured to the orifice of a suction tube to prevent injury that may occur, for example, if the tube becomes rigidly attached to an internal body structure or tissue. The term "surgical sponge" further includes any other similar absorbent device such as a wound dressing and an absorbent device attached to a holder, such as an absorbent swab.

The term "surgical instrument" as used herein means any rigid or semi-rigid implement inserted through a surgical incision or wound into a cavity in an area requiring surgical treatment. Such an item typically is manipulated by a surgeon in carrying out surgical treatment. A wide variety of surgical instruments are known, including, but not limited to, cutting devices such as scissors, scalpels, and drills; holding and clamping devices such as forceps, hemostats, and retractors; and other miscellaneous items such as probes, suction tubes, and suture holders.

The surgical item and marker of the invention are adapted for use in conjunction with an electronic article surveillance (EAS) system. An EAS system generally comprises: means for generating within an interrogation zone an interrogating field; a marker responsive to the presence of the interrogating field; detection means for detecting the response of the marker; and indicating means for alerting a system user to the presence of the marker. The present method and article may be employed in conjunction with any EAS system having these attributes and capable of being operated in the context of a medical facility.

It will be understood that while the present invention is described in connection with the treatment of humans, the articles and methods set forth herein may be applied in the veterinary treatment of animals as well.

In an aspect of the invention there is provided a marker that exhibits mechanical resonance at a resonant frequency in response to the incidence thereon of an alternating electromagnetic interrogating field, whereby the marker is provided with a signal-identifying characteristic. Preferably, the resonant frequency ranges from about 70 to 300 kHz. The system further comprises an interrogating means for generating an electromagnetic interrogating field having a preselected interrogating frequency modulated as a series of pulses; a detecting means for detecting the signal-identifying characteristic; and an indication means activated by the detecting means in response to the detection of the signal-identifying characteristic, which is preferably a ring-down of the electromagnetic dipole field emanating from the resonant marker. The marker preferably comprises: (i) a magnetomechanical element, preferably having one or more elongated strips of amorphous metal alloy; (ii) a bias means, preferably a bias magnet disposed within the marker, that applies a biasing magnetic field to the magnetomechanical element, whereby the marker is armed for resonance; and (iii) a housing enclosing the magnetomechanical element and the bias means, wherein the magnetomechanical element is free to mechanically vibrate at its mechanical resonant frequency. The housing preferably comprises one or more means for attaching the marker to a surgical or other item. It is further preferred that the marker comprise a plurality of elongated strips, increasing the signal generated during resonance and/or providing the marker with sensitivity to excitation by interrogating fields directed in a plurality of orientations relative to the marker.

The present invention also provides a method for detecting a surgical implement left within a patient after surgery, comprising the steps of: (i) attaching a marker to the surgical implement prior to its use during the surgery, the marker comprising at least one magnetomechanical element that exhibits mechanical resonance at a resonant frequency in the presence of an electromagnetic interrogating field, the resonant frequency ranging from about 70 to 300 kHz, whereby the marker is provided with a signal-identifying characteristic; (ii) placing a surgical implement detector proximate an operating room, the detector being adapted to generate the electromagnetic interrogating field and detect the signal-identifying characteristic; (iii) subjecting said patient after said surgery to said electromagnetic interrogating field generated by the surgical implement detector; (iv) detecting the signal-identifying characteristic; and (v) activating an indication means in response to the detection of the signal-identifying characteristic, whereby the presence of the implement is indicated to the attending medical personnel. Suitable measures may then be taken to assure that proper treatment is given to the patient.

Various advantages attend one or more embodiments of the present invention. By virtue of the increase in resonant operating frequency from that of conventional magnetomechanically resonant tags, the present invention affords smaller, more compact tags that are attachable to a larger range of surgical implements without compromising their intended functionality or impeding the surgeon performing the operation. The increased frequency also reduces or eliminates the possibility of false alarms and missed item detection. Detection sensitivity is enhanced and detection accuracy is increased. Certain electronic noise sources generate electromagnetic interference that must be distinguished by the detection electronics from legitimate signals produced by actual activated markers. The increase in operating frequency in the present system enhances the detection reliability.

Markers in accordance with certain aspects of the invention are sensitive to interrogating fields having a wider spread of orientation than conventional markers, making it highly unlikely that a marker of the invention passing through an interrogation zone would escape detection. In light of the aforesaid advantages, systems incorporating the markers of the invention are inexpensive to construct and maintain, easy to use and operate in an accurate, reliable manner.

BRIEF DESCRIPTION OF THE DRAWINGS

The invention will be more fully understood and further advantages will become apparent when reference is had to the following detailed description of the preferred embodiment of the invention and the accompanying drawings, in which.

DESCRIPTION OF THE PREFERRED EMBODIMENTS

The present invention provides a system capable of detecting surgical implements left within a patient during surgery. The system relies on attachment of an externally detectable marker to a surgical implement, which may be any of a wide variety of devices appointed to be placed into a surgical wound cavity during a surgical procedure, typically including sponges, gauzes, instruments, probes, and various cutting, holding, and clamping devices. The remote detectability of the marker allows detection and removal of the implement prior to completion of the surgery, thereby eliminating the severe consequences that arise from retained articles.

The marker employed in the present system is magnetomechanically resonant. That is to say, the marker comprises at least one magnetomechanical element which, in the presence of a suitable alternating electromagnetic field, is caused to mechanically vibrate at a frequency which is a natural resonant frequency of the element. The vibration causes a dipolar electromagnetic field to emanate from the marker, thereby providing the marker with a signal-identifying characteristic.

Figure 1:
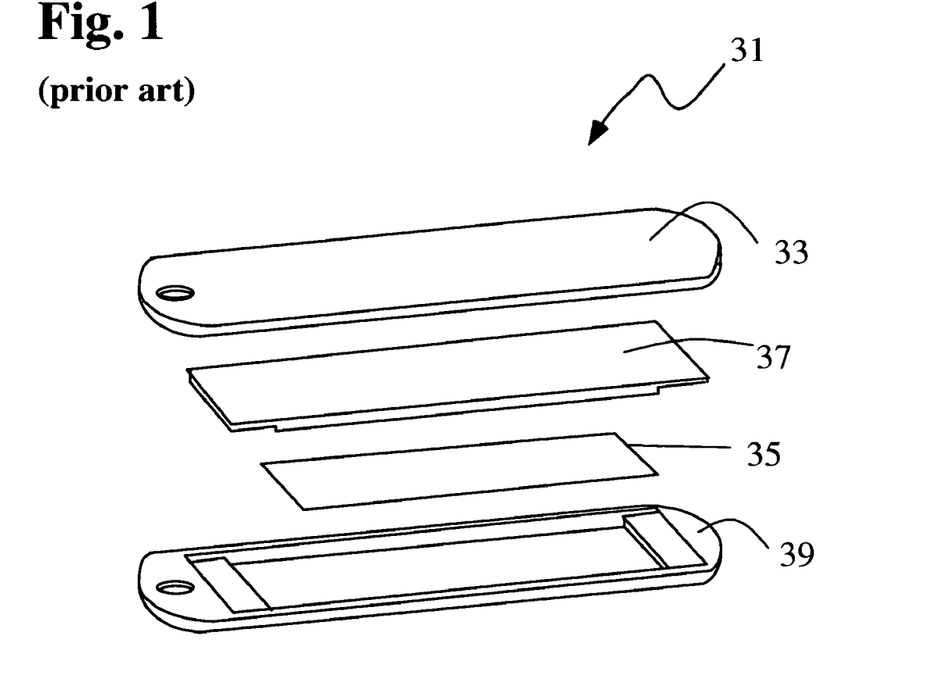
FIG. 1 is a perspective view depicting a conventional marker.

The marker of the surgical implement detector system of the invention is activated in response to the incidence thereon of a suitable alternating electromagnetic interrogating field generated by an interrogating means. Preferably the interrogating field is provided as a preselected interrogating frequency, modulated as a series of pulses. Optionally, the interrogating frequency is swept through a preselected range encompassing the resonant frequency of the tag, to ensure that the resonance is excited. The magnetomechanical element of the marker is urged to resonance during each pulse. After each pulse is completed, the energy stored in the magnetomechanically resonating element decays. As a result, the marker dipole field emanating from the marker decays or rings down correspondingly. The amplitude of the alternating field generally remains within an envelope that decays exponentially, affording the marker a signal-identifying characteristic that is detectable by a detecting means. The detection of this ring-down in synchrony with the activation of the marker by the interrogating field provides a preferred way of reliably discriminating the marker's response from other ambient electronic noise or the response of other nearby ferrous objects which are not resonantly excited. An indication means is operably associated with the detecting means and is activated in response to the detection of the signal-identifying characteristic by the detecting means. Preferably the indication means is a visible or audible alarm that signals and thereby alerts the surgical staff to the presence of a retained surgical implement, allowing timely intervention and removal of the offending object, and averting untoward medical consequences for the patient Referring now to FIG. 1 there is depicted generally a prior art marker 31 having as a magnetomechanical element a strip 35 of amorphous metal about 4 cm long. A housing comprises a bottom section 39 having a cavity to accommodate strip 35 and a cover section 33. A bias magnet 37 is located in proximity to strip 35.

The marker of the invention is preferably housed in a housing comprising a rigid or semi-rigid plastic material. In other aspects of the invention parts or all of the housing may be integrally formed in a surgical implement. The housing has a cavity in which the magnetomechanical element is accommodated in a manner that permits it to vibrate freely. A variety of manufacturing methods are suitable for producing the housing, including casting, molding by vacuum or injection techniques, and folding of sheet-form materials. The marker may further comprise additional cavities wherein the one or more bias magnets are disposed. The housing may be provided with apertures or other structures facilitating attachment of the marker to a surgical implement. For example, a rivet, screw, lanyard, or adhesive may be used for the attachment.

In an embodiment of the invention, the marker has a magnetomechanical element comprising at least one elongated strip of a magnetostrictive amorphous metal alloy. As used in this specification and the appended claims, the term "strip" includes forms such as wire, ribbon, and sheet. By elongated strip is meant an object with a geometrical form having a characteristic elongated length direction or orientation and a characteristic thin direction perpendicular to the length direction, with the dimension of the object along the elongated direction substantially greater than the dimension along the thin direction. Preferably the ratio of the dimensions is at least 100:1. For example, the thin direction in a cylindrical wire is along a diameter of the wire, while the long direction is along the cylindrical axis. A generally planar sheet or ribbon has a small thickness direction normal to the plane and a length direction in-plane. Preferably a rectangular sheet used in the marker of the invention has a long direction in-plane that is at least five times the in-plane width direction perpendicular thereto. Those skilled in the art will recognize that an elongated strip as defined herein possesses a low demagnetizing factor for magnetization along the elongated direction.

A variety of magnetostrictive amorphous metal alloy ribbons are useful in the construction of the marker of the present invention. Many amorphous metals combine high mechanical hardness and relatively low magnetic anisotropy and loss, leading to low internal friction, a high magnetomechanical coupling factor and magnetomechanical resonance with high Q. One amorphous metal suitable for the present marker consists essentially of an alloy having 40% Fe, 38% Ni, 4% Mo, and 18% B (atomic percentages) plus incidental impurities. Other amorphous metal alloys exhibiting desirable magnetomechanical behavior are also useful in the present marker.

The marker is further provided with a bias means that provides a magnetic field to bias the magnetomechanical element and thereby arm it to resonate. The bias means may comprise one or more magnetized elements composed of permanent (hard) magnetic material or semi-hard magnetic material. Preferably magnetic material of either type has a magnetic coercivity sufficient to prevent the material from becoming demagnetized due to inadvertent exposure to other magnetic fields. A wide variety of magnetic materials are suitable. High anisotropy, high coercivity materials, such as ferrites and rare-earth magnets, may be provided as magnets having a short aspect ratio, i.e., a low ratio of the dimensions along the magnetization direction and in a perpendicular direction. Other materials, such as Arnochrome, vicalloy, and hard steels, are advantageously employed as thin strips, preferably aligned generally parallel to elongated magnetomechanical amorphous strips. In some implementations the bias means may comprise magnetized magnetic powder, such as barium ferrite, which may be dispersed within a polymeric matrix comprising part or all of the marker housing. Other forms by which the bias means may be incorporated in or on the housing will be apparent to persons skilled in the art. In still other implementations the bias field is provided externally by a dc magnetic field from a permanent magnet or an electromagnet.

Figure 2:
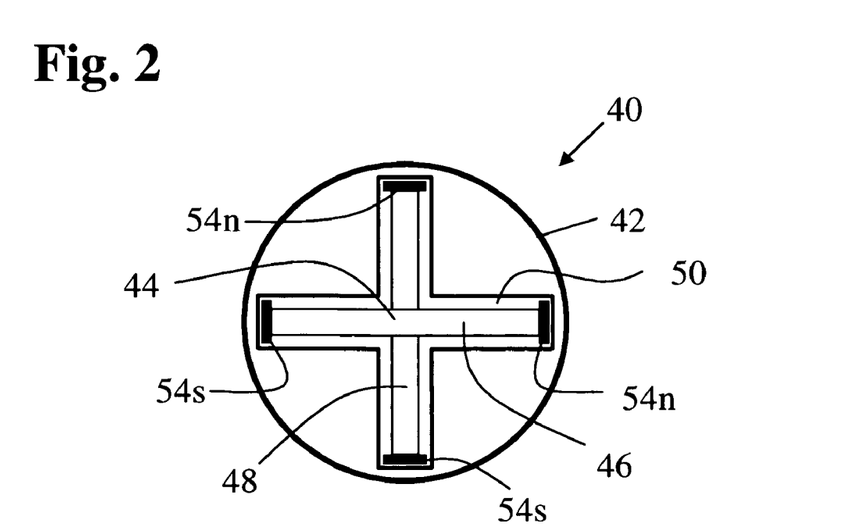
FIG. 2 depicts a partial top view of a marker of the invention having two magnetomechanically resonant, amorphous metal strips.
Figure 3:
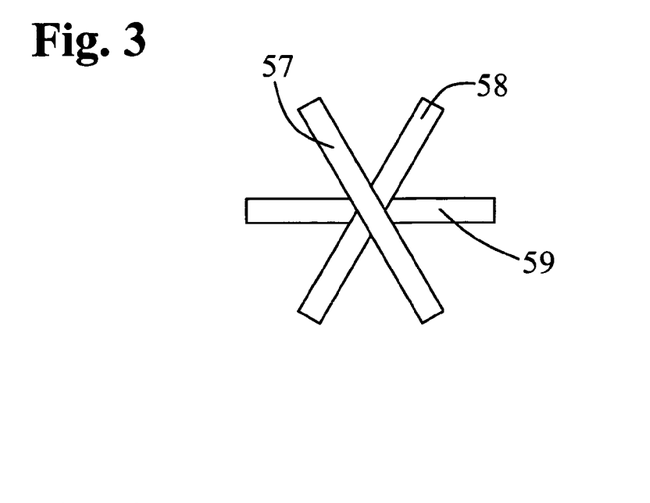
FIG. 3 is a top view depicting part of a marker of the invention employing three elongated amorphous metal strips oriented equi-angularly.

One suitable marker for the practice of the invention has a magnetomechanical element comprising a plurality of elongated strips, preferably composed of amorphous metal, disposed in a non-parallel orientation, i.e., a configuration in which the respective elongated directions of the strips are not parallel. In this aspect it is preferred that the strips are disposed in a stack with their centers generally coincident. FIGS. 2 and 3 depict embodiments of the marker having strips disposed equi-angularly, i.e., with two perpendicularly oriented strips and with three strips at 120° intervals, respectively.

The marker 40 depicted by FIG. 2 is housed in a generally cylindrical, thin, disk-shaped carrier 42. A magnetomechanical element 44 comprises first elongated strip 46 and second elongated strip 48, both being composed of a ribbon of amorphous metal alloy. The ribbons are disposed in cavity 50 of housing 42 with their elongated directions substantially perpendicular, their centers substantially coincident, and their planes substantially parallel. Cavity 50 is sized and shaped to accommodate ribbons 46, 48 and allow them to vibrate freely. A bias means whereby magnetomechanical element 44 is armed to resonate is provided by magnets 54n and 54s, each of which has a north pole and a south pole. A magnet 54n and a magnet 54s are disposed at opposite ends of ribbon 46. Magnet 54n has its north pole proximate one end of first ribbon 46, while magnet 54s has its south pole proximate the other end of first ribbon 46. A magnet 54n and a magnet 54s are similarly disposed at opposite ends of second ribbon 48. A cylindrical cover (not shown) having the form of a disk with a diameter matching that of carrier 42 and affixed thereon seals the marker and the components therein. The attachment of the cover may be accomplished by adhesive, welding, a mechanical snap fit, a fastener such as a rivet or screw, or other means apparent to one skilled in the art.

FIG. 3 depicts a configuration for use in a marker of the invention in which three substantially similar, magnetostrictive amorphous metal strips 57, 58, 59 are oriented equiangularly with their centers substantially coincident. The planes of the strips are substantially parallel. The ribbons are disposed in a suitable housing (not shown) similar to that depicted by FIG. 2, but having three cavities oriented at equally spaced angles, instead of the two cavities seen in FIG. 2. One suitable bias means is similar to that used with the embodiment of FIG. 2, comprising magnets of opposite polarity at the respective ends of each strip.

A number of advantages are conveyed by the use of markers having plural strips. The strength of the dipole field radiated by the marker in resonance increases in rough proportion to the volume of resonating material. The signal available for detection is in general increased by use of markers having more magnetomechanical material, thereby enhancing the reliability of the detection system in identifying the presence of a marked surgical implement. In addition, the increased signal significantly improves detection accuracy, and hence the level of protection afforded the surgical patient. Further, a marker of the present invention with strips having more than one orientation is readily excited by interrogating fields that range widely in vector direction. Since at least one of the directions in which the marker is most sensitive is inevitably oriented sufficiently close to the direction of the interrogating field that the tag encounters, it is even less likely that the marker would pass through an interrogation zone without being detected,. On the other hand, markers comprising a single elongated strip are most sensitive to excitation by an interrogating field having a strong vector component along a single preferred marker orientation, in most cases the elongated direction of the strip. Even though the interrogating field may vary in both magnitude and direction as a function of position within the interrogation zone, a marker fortuitously oriented in an unfavorable direction has a small chance of never being excited while traversing the interrogation zone. While this possibility is remote, a marker sensitive to interrogation fields in more than one orientation by virtue of having differently oriented elements is nonetheless preferred for use in the present system to provide enhanced reliability and detectability.

Figure 4:
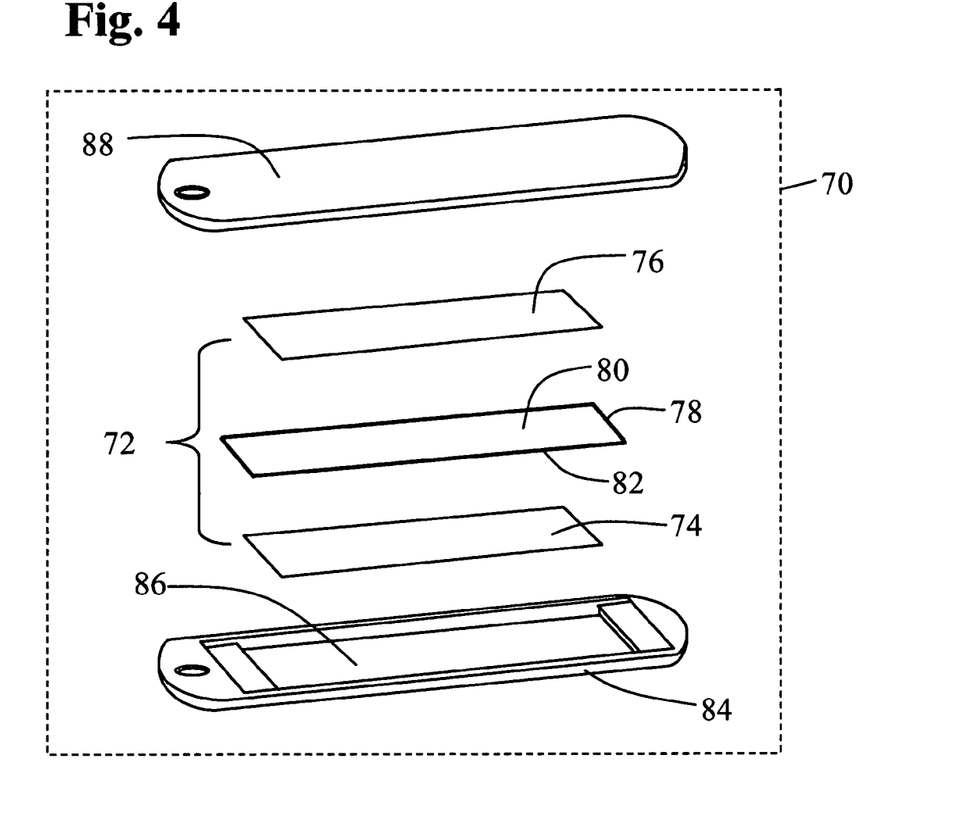
FIG. 4 is an expanded, perspective view depicting a marker of the invention having two magnetomechanically resonant strips surrounding a bias magnet strip.

In another aspect of the invention depicted by FIG. 4, the magnetomechanical element 72 of marker 70 comprises a first elongated strip 74 and a second elongated strip 76, preferably composed of amorphous metal. The marker further comprises a bias magnet disposed between the alloy strips. Preferably the bias magnet takes the form of a strip 78 having a top side 80 and a bottom side 82, as depicted by FIG. 4. The strips are oriented with their length directions substantially parallel. In addition, the planes of the strips are substantially parallel. The housing comprises a bottom section 84 having a cavity 86 and a top section 88, in which the magnetomechanical strips are free to vibrate. In this configuration, the symmetrical disposition of the magnetomechanical strips advantageously results in application of a biasing magnetic field that is of substantially equal magnitude for each. As a result, the resonant frequencies of the strips are substantially equal, and the resonances of the strips are thus easily excited in concert by a common interrogating field. Therefore, such a marker, having a greater volume of resonating material than a prior art marker with but a single elongated strip, will in most cases deliver an enhanced signal strength.

It is further preferred that the magnetomechanical element of the present marker resonate at a high frequency. Conventional magnetomechanical article surveillance systems employ markers resonant at frequencies of 50 to 60 kHz. Significant advantages attend systems using markers resonant at higher frequencies and comprising one or more elongated strips of amorphous metal. Many commonly encountered sources of electronic noise have a 1/f frequency spectrum, so less noise is present at higher frequencies. More importantly, the resonant frequency of an elongated strip is approximately inversely proportional to the strip's length. Increasing the chosen resonant frequency thus allows use of shorter strips in constructing the marker for the system of the invention. As a result, the entire marker may be made advantageously smaller. Beneficially the marker of the invention uses a smaller amount of the relatively expensive amorphous metal strip and bias magnetic material. More importantly, surgical items too small to accommodate existing markers may be tagged using the present marker. Moreover, markers of decreased size are far less likely to compromise the functionality of a marked surgical item or to unduly restrict the ability of the surgeon or other assistant to see and access the operation site and to manipulate and use the item in an optimal manner for its intended primary function.

For example, sponges of a variety of sizes are widely used in the course of surgery. Most commonly, the sizes used range from about 45 cm square down to 10 cm square or less. It is preferred that a marker be used that is small in comparison to the size of the item being monitored. Markers used with conventional electronic article surveillance systems frequently are over 4 cm long and 1-1.5 cm wide. Markers of this size are especially likely to impair the functionality of sponges that are 10 cm square or smaller, yet are even more prone to being overlooked than larger sponges. In addition, many implements such as hemostats are not readily tagged with markers of the conventional size. Advantageously, markers of the invention that are resonant at 120 kHz or more are about half the length of conventional markers or less, yet provide adequate signal for detection. A single detection system sensitive to the present marker is thus readily adapted for identifying a much wider variety of surgical items than existing systems.

A preferred marker of the invention is resonant at a frequency ranging from about 70 to 300 kHz. The markers disclosed by prior art workers are typically about 4 cm long. This length is constrained principally by the length of an amorphous strip that exhibits a magnetomechanical resonance at an operating frequency preselected in the range of 50 to 60 kHz. The amorphous metal ribbon used conventionally is typically between 4 and 12 mm wide. The higher resonant frequency of the present marker allows it to be correspondingly shorter, thereby allowing tagging of items heretofore not amenable to such protection. Advantageously, an increase to 120 kHz allows a marker to be shortened to about 2 cm, or less than 1 inch. However, the shortened marker also needs to use correspondingly narrower ribbon to maintain a similar demagnetizing factor and definition of its characteristic modes of resonant vibration. Preferably, the marker of the invention comprises a rectangular ribbon having an aspect ratio, i.e. a ratio of length to width, of at least about 4:1. More preferably the aspect ratio is at least 8:1. It is preferred that at least the same dimensional ratios be maintained for elongated strips of other forms, e.g. wire. Without being bound to any particular theory, it is believed that maintaining the same aspect ratio of length to width for rectangular ribbon of constant thickness results in an amorphous strip having a volume that decreases approximately with the square of the operating frequency, with a concomitant loss of signal strength as discussed hereinabove in greater detail. This decrease, along with the need for tighter dimensional control in tag manufacture and the generally faster ring-down in structures resonating at higher frequencies, makes it preferable for the resonant frequency not to exceed about 300 kHz and for the marker to comprise plural strips to increase the radiated resonant signal. An excessively high resonant frequency also impinges on other sources of electromagnetic noise, such as the 455 kHz intermediate frequency of conventional superheterodyne AM broadcast receivers. A 300 kHz marker will have a length about one fifth that of a conventional marker, allowing a very wide range of implements to be tagged. More preferably, the resonant frequency ranges from about 110 to 250 kHz, permitting the marker to be significantly shorter than conventional markers, yet have sufficient magnetic material for detectability and consistent manufacture. Still more preferably, the marker has a resonant frequency ranging from about 120 to 200 kHz.

Many markers suitable for use in the practice of the present invention comprise an active element that is encased in a plastic housing comprising some means allowing the marker to be attached to another item. A suitable housing also allows the marker to be sterilized in a manner appropriate for its intended surgical use. The term "marker" as used herein refers generically to the combination of the magnetomechanically active element, any required bias means, and a housing that may provide structures needed for mounting or affixing the marker to an article. In addition, it will be understood that a marker may further include one or more active elements responsive to article surveillance systems of different types. It will also be appreciated that more than one marker may be attached to a given surgical item to further improve its detectability or to allow detection by EAS systems of different types.

Figure 5:
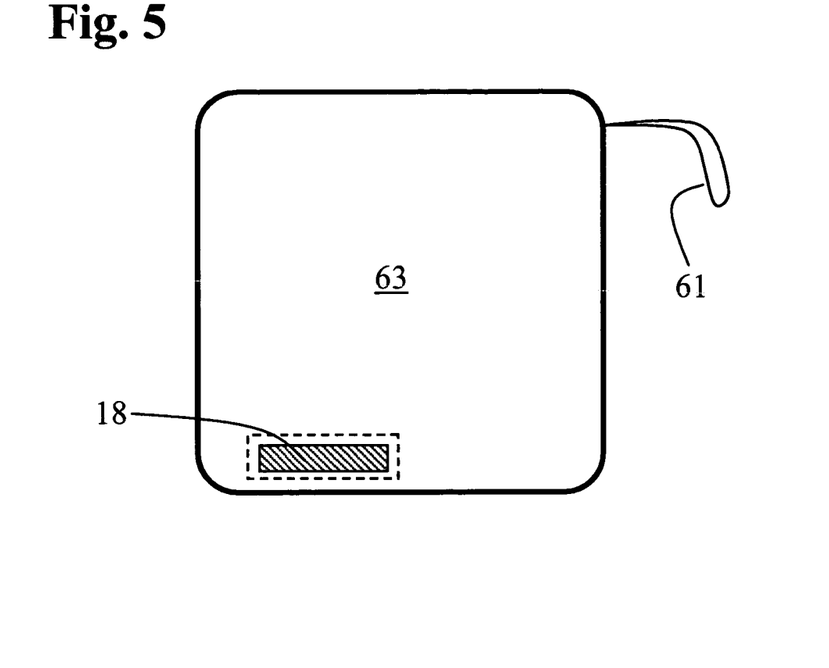
FIG. 5 is a frontal view depicting a surgical sponge with a marker sewn into its corner in accordance with the invention.
Figure 6:
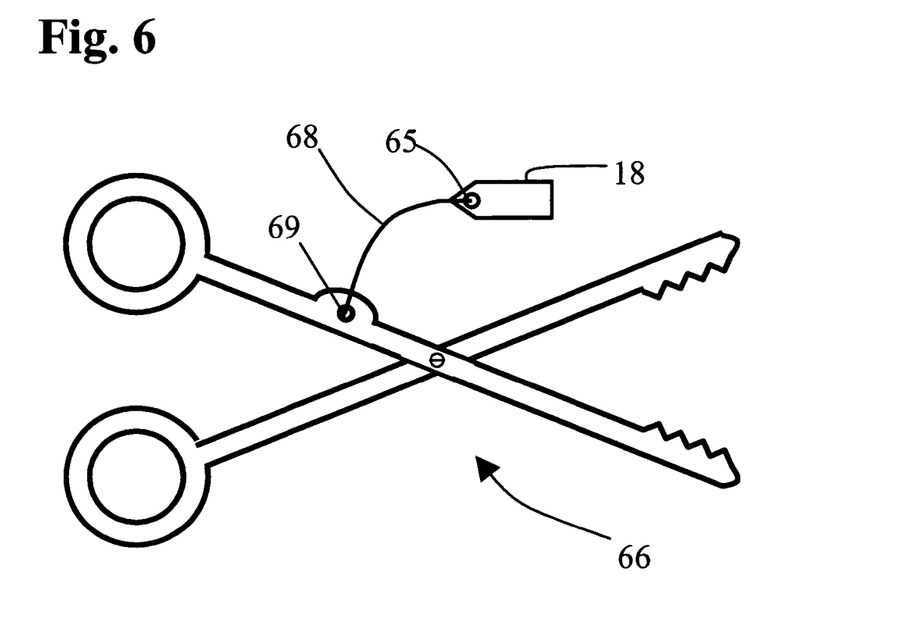
FIG. 6 is a perspective view depicting a surgical forceps of the invention having a marker attached thereto by a lanyard.

Referring now to FIGS. 5 and 6 there are depicted, respectively, a surgical sponge 63 and a surgical forceps 66 to which are attached a magnetomechanical marker 18 in accordance with the invention. The attachment may be carried out by any suitable means. Preferably the attachment does not compromise the use of the item for its intended function. As depicted, the marker is sewn into a corner of sponge 63, which also includes a loop 61 of thread or cord to facilitate location and removal of the sponge following its use. Lanyard 68 threaded through an eyelet 65 in marker 18 is used to attach the marker to a hole 69 in the handle of forceps 66. Other attachment means useful in the practice of the invention will be apparent to one skilled in the art.

The surgical instrument detection system of the present invention is advantageously used in carrying out a wide variety of medical and surgical procedures on a patient. Preferably, the requisite surgical implement detection electronics system is proximate the operating room appointed for surgical procedures to be carried out. For example, the detection electronics may be placed inside the operating room so that a scan may conveniently be carried out at any point during the surgical procedure. Alternatively, the system is placed in the vicinity of the operating room, such as in the hallway of the operating room suite, so that the patient may be scanned while in transit to the recovery room following surgery.

Figure 7:
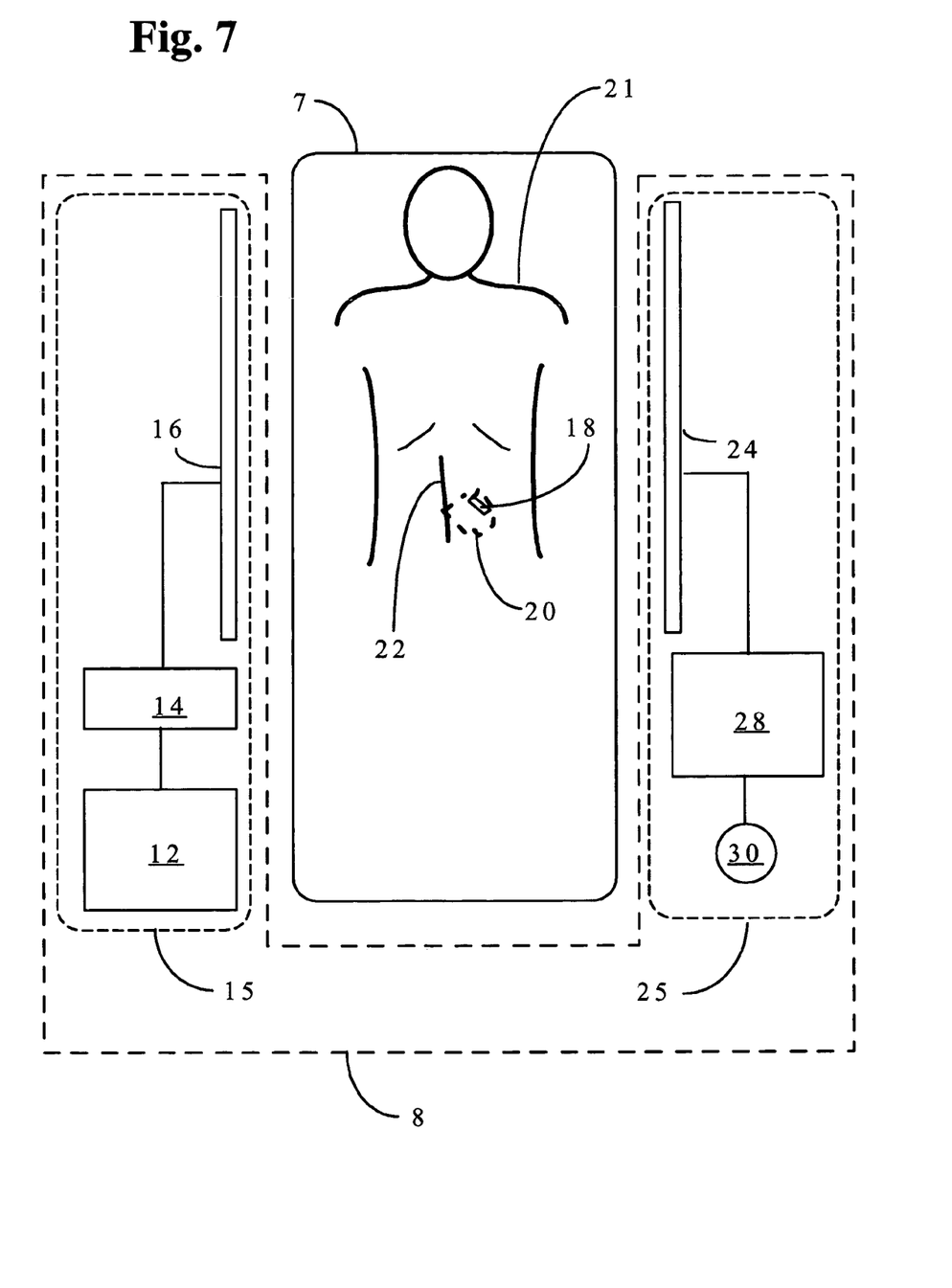
FIG. 7 is a block diagram depicting a gurney with a surgical patient in the interrogation zone of a surgical implement detector system of the invention.

FIG. 7 depicts one implementation of the method of the invention for scanning patient 21 situated on a surgical gurney 7. Surgical instrument detection system 8 is used to scan the patient 21 after completion of surgery for the presence of a marker 18 affixed to surgical item 20 inadvertently left within the patient after a procedure carried out through incision 22. At any time during or after such a procedure, the patient is exposed to an interrogating field produced by interrogating means 15 comprised of frequency generating means 12, field-changing means 14, and field generating means 16. Frequency generating means 12 generates a preselected frequency encompassing the resonant frequency of marker 18 and supplies the power signal to energize the field generating means 16. Either a single frequency waveform may be generated or the frequency may be chirped, that is, swept within a preselected range of frequencies encompassing the frequency of interest. Field generating means 16 comprises at least one, and preferably a plurality of antenna elements, used to produce the requisite electromagnetic interrogating field. Marker 18 responds resonantly to the interrogating field, which is preferably a series of pulses modulating the resonant frequency of marker 18, with the emission of a marker dipole field.

System 8 further comprises receiving means 25, including detecting electronics 28, detecting antenna 24, and indicating means 30. Detecting antenna 24 comprises at least one, and preferably a plurality of receiver elements, which are preferably coils or monopole or dipole antennas. The receiving elements are connected to detecting electronics 28, which senses the presence of the signal-identifying characteristic of marker 18, such as a ring-down of the marker dipole field. It will be understood by those skilled in the art that some implementations of the present invention will employ the same antenna elements for both field generation and receiving functions. Indication means 30 is operably connected to detecting electronics 28 and comprises a source of distinctive sound or light activated upon detection of the signal-identifying characteristic of a marker associated with a retained surgical item. The signal alerts relevant personnel so that followup medical intervention and care can be initiated. Preferably, indicating means 30 is a flashing light. Alternatively indicating means 30 is a buzzer. As a further alternative, indication means 30 comprises a combination light and sound source. The indication means may also further provide a printed record or a message transmitted to a computer system memorializing the detection of a marker.

Preferably, a scan is carried out immediately before a surgical procedure is completed to ensure that all implements have been removed from the patient and properly accounted for. The surgical incision is then closed in the usual way. Moreover, scanning can also be accomplished after completion of a procedure, since a tagged article can be detected even if left within a patient, causing it to be surrounded by normal body tissue and the fluids and other substances found within a patient. Unlike previous methods for ensuring removal of surgical items, such as x-rays, the present method can be carried out quickly and conveniently, even in the rigorous working environment of an operating room. The surgical items and the ancillary equipment, such as the EAS electronics, are compatible with such requirements as proper sterilization and safety appropriate for their respective locations.

Having thus described the invention in rather full detail, it will be understood that such detail need not be strictly adhered to but that various changes and modifications may suggest themselves to one skilled in the art, all falling within the scope of the invention as defined by the subjoined claims.

What is claimed is:

1. A method for detecting a surgical implement left within a patient during surgery in an operating room, comprising the steps of:
   a) attaching a marker to said surgical implement before use during said surgery, said marker comprising a cavity therein and a magnetomechanical element comprising a plurality of elongated strips of magnetostrictive amorphous metal having an aspect ratio of at least about 4:1 and disposed in said cavity in a non-parallel orientation and a bias means for magnetically biasing said magnetomechanical element to arm said element to exhibit mechanical resonance at a resonant frequency in the presence of an electromagnetic interrogating field, said resonant frequency ranging from about 70 to 300 kHz, whereby said marker is provided with a signal-identifying characteristic;
   b) placing a surgical implement detector proximate said operating room, said detector being adapted to generate said electromagnetic interrogating field and detect said signal-identifying characteristic;
   c) subjecting said patient to said electromagnetic interrogating field generated by said surgical implement detector;
   d) detecting said signal-identifying characteristic; and
   e) activating an indication means in response to the detection of said signal-identifying characteristic indicative of the presence of said implement.

2. In a surgical implement, the improvement wherein a magnetomechanical marker detectable by an electronic article surveillance system is attached to the implement, the marker comprising:
   a) a magnetomechanical element comprising one or more elongated strips composed of magnetostrictive amorphous metal alloy and having an aspect ratio of at least about 4:1;
   b) a housing comprising one cavity sized and shaped to accommodate said strips, and said strips being disposed in said one cavity with a non-parallel orientation and able to mechanically vibrate freely therewithin; and
   c) a bias means for magnetically biasing said magnetomechanical element, said magnetomechanical element being armed to resonate at a resonant frequency in the presence of an interrogating electromagnetic field, said resonant frequency ranging from about 70 to 300 kHz.

3. A surgical implement as recited by claim 2, wherein the marker comprises:
   a) a magnetomechanical element comprising a first and a second elongated strip, each strip being composed of magnetostrictive amorphous metal alloy;
   b) a bias magnet magnetically biasing said magnetomechanical element, said bias magnet having a top side and a bottom side;
   c) said first elongated strip being disposed on said top side of said bias magnet and said second elongated strip being disposed on said bottom said of said bias magnet.

4. A surgical implement as recited by claim 2, wherein said aspect ratio is at least about 8:1.

5. A surgical implement detection system, comprising:
   a) a marker comprising:
      i) at least one magnetomechanical element comprising a plurality of elongated strips composed of magnetostrictive amorphous metal alloy, having an aspect ratio of at least about 4:1, and exhibiting magnetomechanical resonance at a resonant frequency ranging from about 70 to 300 kHz and radiating a marker dipole field in response to the incidence thereon of an alternating electromagnetic interrogating field;
      ii) a bias means for magnetically biasing and thereby arming said magnetomechanical element to resonate; and
      iii) a housing including a cavity enclosing said magnetomechanical element and said bias means, said magnetomechanical element being free to mechanically vibrate in said cavity at said resonant frequency, and said elongated strips having a non-parallel orientation and their centers coincident, whereby said marker is provided with a signal-identifying characteristic comprising a ring-down of said dipole field;
   b) an interrogating means for generating said electromagnetic interrogating field having a preselected interrogating frequency, modulated as a series of pulses and being substantially equal to said resonant frequency;
   c) a detecting means for detecting said signal-identifying characteristic; and
   d) an indication means activated by said detecting means in response to the detection of said signal-identifying characteristic.

6. A system as recited by claim 5, wherein: said bias means comprises a bias magnet having a top side and a bottom side; said magnetomechanical element comprises a first elongated strip and a second elongated strip; said first elongated strip is disposed on said top side and said second elongated strip is disposed on said bottom side of said bias magnet; and the planes of said first and second elongated strips are substantially parallel.

7. A system as recited by claim 6, wherein each of said strips has substantially the same resonant frequency.

8. A system as recited by claim 5, wherein said resonance frequency ranges from about 110 to 250 kHz.

9. A system as recited by claim 8, wherein said resonance frequency ranges from about 120 kHz to 200 kHz.

10. A system as recited by claim 9, wherein said aspect ratio is at least about 8:1.

11. A system as recited by claim 8, wherein said aspect ratio is at least about 8:1.

* * * * *